United States Patent [19]

Parg et al.

[11] Patent Number: 4,523,946
[45] Date of Patent: Jun. 18, 1985

[54] SUBSTITUTED 4,5-DIMETHOXYPYRIDAZONES AND THEIR USE FOR CONTROLLING UNDESIRABLE PLANT GROWTH

[75] Inventors: Adolf Parg, Bad Duerkheim; Bruno Wuerzer, Otterstadt; Gerhard Hamprecht, Weinheim, all of Fed. Rep. of Germany

[73] Assignee: BASF Aktiengesellschaft, Fed. Rep. of Germany

[21] Appl. No.: 457,655

[22] Filed: Jan. 13, 1983

[30] Foreign Application Priority Data

Jan. 28, 1982 [DE] Fed. Rep. of Germany ....... 3202678

[51] Int. Cl.$^3$ .................... C07D 237/22; A01N 43/58
[52] U.S. Cl. ........................ 71/092; 544/239; 544/240
[58] Field of Search ............... 544/240, 239; 71/92

[56] References Cited

U.S. PATENT DOCUMENTS 3,326,660  6/1967  Reicheneder et al. ............... 71/2.5
3,697,522  10/1972  Reicheneder et al. ......... 260/250 A
4,360,672  11/1982  Parg et al. .......................... 544/240

FOREIGN PATENT DOCUMENTS 1197676  4/1966  Fed. Rep. of Germany .
1670315  12/1972  Fed. Rep. of Germany .
3013267  10/1981  Fed. Rep. of Germany .

Primary Examiner—Nicholas S. Rizzo
Attorney, Agent, or Firm—Keil & Weinkauf

[57] ABSTRACT

Substituted 4,5-dimethoxypyridazones of the formula

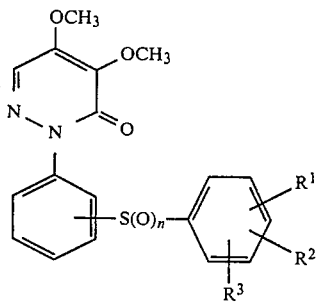

where $R^1$, $R^2$ and $R^3$ independently of one another are each hydrogen, halogen, nitro, cyano, carboxyl, alkyl, haloalkyl, alkoxy, haloalkoxy, alkylmercapto, haloalkylmercapto, alkylsulfinyl or alkylsulfonyl and n is 0, 1 or 2, are used for controlling undesirable plant growth.

12 Claims, No Drawings

SUBSTITUTED 4,5-DIMETHOXYPYRIDAZONES AND THEIR USE FOR CONTROLLING UNDESIRABLE PLANT GROWTH

The present invention relates to 4,5-dimethoxypyridazones, herbicides containing these compounds as active ingredients, and a method of controlling undesirable plant growth with these compounds.

It has been disclosed that 1-phenyl-4,5-dimethoxypyridazin-6-ones (German Pat. No. 1,197,676 and German Laid-Open Application No. DOS 3,013,267) and 1-phenyl-4-methoxy-5-halopyridazin-6-ones (German Pat. No. 1,670,315) possess herbicidal activity.

We have found that substituted 4,5-dimethoxypyridazones of the formula

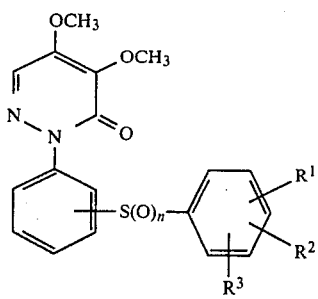

where $R^1$, $R^2$ and $R^3$ independently of one another are each hydrogen, halogen, nitro, cyano, carboxyl, alkyl, haloalkyl, alkoxy, haloalkoxy, alkylmercapto, haloalkylmercapto, alkylsulfinyl or alkylsulfonyl, each of 1 to 4 carbon atoms, and n is 0, 1 or 2, possess good herbicidal activity and, surprisingly, are tolerated by crops, or exhibit selective herbicidal activity when used in crop cultivation.

$R^1$, $R^2$ and $R^3$ independently of one another can each be, for example, hydrogen, fluorine, chlorine, bromine, iodine, nitro, cyano, carboxyl, methyl, ethyl, n-propyl, i-propyl, n-butyl, tert.-butyl, trifluoromethyl, difluoromethyl, fluoromethyl, trichloromethyl, dichloromethyl, chloromethyl, difluorochloromethyl, 1-chloroethyl, 2-chloroethyl, 1-fluoroethyl, 2-fluoroethyl, 2,2,2-trichloroethyl, 2,2,2-trifluoroethyl, 1,1,2,2-tetrafluoroethyl, 1,1,2-trifluoro-2-chloroethyl, 1,1,2,2,2-pentafluoroethyl, methoxy, ethoxy, n-propoxy, i-propoxy, tert.-butoxy, trichloromethoxy, trifluoromethoxy, 1-chloroethoxy, 2-chloroethoxy, 1-fluoroethoxy, 2-fluoroethoxy, 2,2,2-trichloroethoxy, 2,2,2-trifluoroethoxy, 1,1,2,2-tetrafluoroethoxy, 1,1,2,2,2-pentafluoroethoxy, methylmercapto, ethylmercapto, trichloromethylmercapto, trifluoromethylmercapto, methylsulfinyl, ethylsulfinyl, methylsulfonyl or ethylsulfonyl, and are preferably in the 2,4,6-, 3,4,6-, or 3,4,5- position with respect to the position of bonding of the phenyl radical having the sulfur bridge.

Preferred compounds are those in which

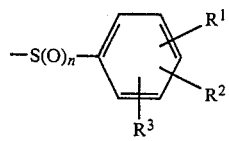

is in the 3- or 4- position on the phenyl ring, and $R^1$, $R^2$ and $R^3$ are each hydrogen, fluorine, chlorine or trifluoromethyl.

The pyridazones of the formula I can be obtained by a process in which a 4,5-dihalopyridazone of the formula

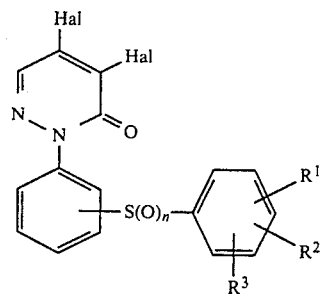

where $R^1$, $R^2$, $R^3$ and n have the above meanings and Hal is halogen, in particular chlorine or bromine, is reacted with about the stoichiometric amount of an alkali metal methylate, in the presence of an organic solvent, in general at not more than 100° C., under atmospheric or superatmospheric pressure (from 1 to 10 bar), the reaction being carried out either continuously or batchwise.

If 1-[3'-(2''-chloro-4''-trifluoromethylphenylthio)-phenyl]-4,5-dichloropyridaz-6-one and sodium methylate are used as starting materials, the course of the reaction can be represented by the following equation:

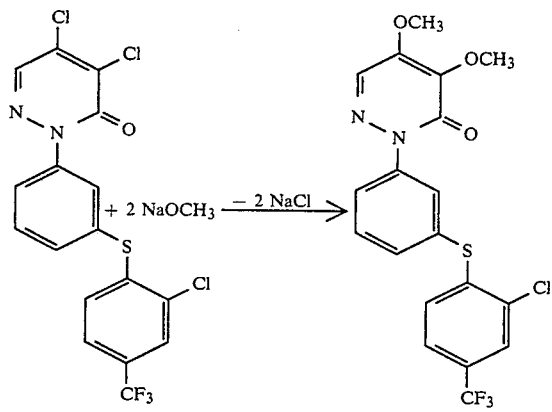

Advantageously, the dihalopyridazone II is first dissolved or suspended in an organic solvent, e.g. toluene, and then reacted with an appropriate amount of the alcoholate. The reaction is carried out under atmospheric or superatmospheric pressure, in general in the course of 12 hours at not more than 100° C., preferably from 40° to 80° C., either batchwise or continuously. The reaction mixture is worked up in a conventional manner. If the end product is obtained in solid form, it is isolated, for example, by filtering off the precipitate under suction, whereas if the end product is obtained in solution in the solvent, the latter is distilled off under reduced pressure, the residue is stirred with water, and the product is filtered off under suction. The product can be purified by, for example, recrystallization or chromatography.

Dihalopyridazones of the formula II which are suitable for use are obtained, for example, by reacting a phenylhydrazine of the formula

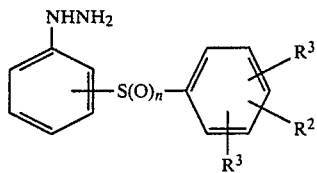

where $R^1$, $R^2$, $R^3$ and n have the above meanings, with a 3-formyl-2,3-dihaloacrylic acid

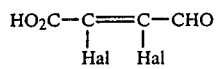

in which Hal is chlorine or bromine.

The reaction to give the corresponding dihalo-acid semicarbazone is carried out at room temperature, for example in an aqueous solution containing a mineral acid, or in a water-containing or anhydrous organic solvent, e.g. ethanol, which is evaporated off after the reaction is complete, and the product, preferably without being isolated, is cyclized by boiling in glacial acetic acid or acetic anhydride, or by heating in an aqueous mineral acid, e.g. hydrochloric acid, at a sufficiently high temperature of not more than 100° C., or by stirring in a concentrated mineral acid, e.g. sulfuric acid, at room temperature, to give the corresponding compound II (German Laid-Open Application Nos. DOS 1,695,840, DOS 2,526,643 and DOS 1,545,595). The reaction may be carried out batchwise or continuously, and the product obtained worked up by a conventional method.

The phenylhydrazines of the formula III which are required can in turn also be obtained by conventional methods from the corresponding anilines by diazotization and reduction (Houben-Weyl, Methoden der organischen Chemie, Volume 10/2, page 180, Georg-Thieme-Verlag, Stuttgart, 1967). Conversion to the corresponding pyrazone can be carried out without isolating the hydrazine, but purer products are obtained if the phenylhydrazine is isolated beforehand as the hydrochloride.

The 4-phenylthioanilines can be obtained by the processes described in German Laid-Open Application No. DOS 2,120,708, while the 3-phenylthioanilines are obtainable by the method described in the European Laid-Open Specification No. EP-OS 29,123.

The oxidation of thioethers to the corresponding sulfoxides or sulfones is well known and does not require explanation.

EXAMPLE 1

(a) A suspension of 30.4 g of 3-(2'-chloro-4'-trifluoromethylphenylthio)-aniline in 200 ml of glacial acetic acid and 25 ml of concentrated hydrochloric acid was reacted with a solution of 6.9 g of sodium nitrite in 17.5 g of water, at from 10° to 20° C., and a solution of 45 g of SnCl$_2$ in 31 ml of 37% strength aqueous hydrochloric acid was then added, the corresponding hydrazine being formed. 16.7 g of mucochloric acid were added, after which the hydrazine-containing solution was stirred for 10 minutes at the boil and then cooled, and 1000 ml of water were added. The oily residue was dissolved in methylene chloride, the solution was dried with magnesium sulfate and evaporated down under reduced pressure, and the residue was chromatographed over silica gel (mobile phase 70:30 toluene/acetone). 38.9 g (86% of theory) of 1-[3'-(2''-chloro-4''-trifluoromethylphenylthio)-phenyl]-4,5-dichloropyridaz-6-one (refractive index $n_D^{25} = 6053$) were obtained.

(b) A suspension of 20 g of 1-[3'-(2''-chloro-4''-trifluoromethylphenylthio)-phenyl]-4,5-dichloropyridaz-6-one, 5.3 g of sodium methylate and 0.1 g of N-methylpyrrolidone in 150 ml of absolute toluene was kept at 60° C. for 2 hours, while stirring. The solution formed was diluted with 200 ml of ether, treated with twice 100 ml of water, dried, filtered and evaporated down under reduced pressure. The oily residue was triturated with diisopropyl ether, and the product was filtered off under suction. 15.7 g (80% of theory) of 1-[3'-(2''-chloro-4''-trifluoromethylphenylthio)-phenyl]-4,5-dimethoxypyridaz-6-one of melting point 86° to 90° C. were obtained.

EXAMPLE 2

A solution of 15 g of the pyridazone obtained as described in Example 1 and 7 g of 85% strength metachloroperbenzoic acid in 200 ml of chloroform was stirred at room temperature for 24 hours, after which it was extracted twice with 100 ml of saturated aqueous sodium bicarbonate solution, dried, filtered and evaporated to dryness under reduced pressure. 14.9 g (96% of theory) of 1-[3'-(2''-chloro-4''-trifluoromethylphenylsulfinyl)-phenyl]-4,5-dimethoxypyridaz-6-one of melting point 126°–130° C. were obtained.

The compounds listed in Table 1 below were prepared or may be prepared by a method similar to that described in Example 1 or 2 above.

| Ex. no. | Position of S | n | $R^3$ | m.p [°C.], $n_D^{25}$ Wavelength of a band in the infrared spectrum |
|---|---|---|---|---|
| 3 | 3 | 2 | 2-chloro-4-trifluoromethylphenyl | SO$_2$ = 1320 cm$^{-1}$ |
| 4 | 4 | 0 | 2-chloro-4-trifluoromethylphenyl | |
| 5 | 4 | 1 | 2-chloro-4-trifluoromethylphenyl | |
| 6 | 4 | 2 | 2-chloro-4-trifluoromethylphenyl | |
| 7 | 3 | 0 | 3-chloro-4-trifluoromethylphenyl | 85–92 |
| 8 | 3 | 1 | 3-chloro-4-trifluoromethylphenyl | |
| 9 | 3 | 2 | 3-chloro-4-trifluoromethylphenyl | |
| 10 | 4 | 0 | 3-chloro-4-trifluoromethylphenyl | 1.6173 |
| 11 | 4 | 1 | 3-chloro-4-trifluoromethylphenyl | |
| 12 | 4 | 2 | 3-chloro-4-trifluoromethylphenyl | |
| 13 | 3 | 0 | 4-chloro-3-trifluoromethylphenyl | |
| 14 | 3 | 1 | 4-chloro-3-trifluoromethylphenyl | |
| 15 | 3 | 2 | 4-chloro-3-trifluoromethylphenyl | |
| 16 | 4 | 0 | 4-chloro-3-trifluoromethylphenyl | |
| 17 | 4 | 1 | 4-chloro-3-trifluoromethylphenyl | |
| 18 | 4 | 2 | 4-chloro-3-trifluoromethylphenyl | |
| 19 | 3 | 0 | 4-trifluoromethylphenyl | |
| 20 | 4 | 0 | 3-trifluoromethylphenyl | 50–55 |
| 21 | 4 | 1 | 3-trifluoromethylphenyl | |

-continued

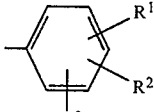

| Ex. no. | Position of S | n | R³ | m.p [°C.], n_D^{25} Wavelength of a band in the infrared spectrum |
|---|---|---|---|---|
| 22 | 4 | 2 | 3-trifluoromethylphenyl | |
| 23 | 3 | 0 | 2-bromo-4-trifluormethylphenyl | |
| 24 | 3 | 1 | 2-bromo-4-trifluormethylphenyl | |
| 25 | 3 | 2 | 2-bromo-4-trifluormethylphenyl | |
| 26 | 3 | 0 | 2,6-dichloro-4-trifluoromethylphenyl | |
| 27 | 3 | 1 | 2,6-dichloro-4-trifluoromethylphenyl | |
| 28 | 3 | 2 | 2,6-dichloro-4-trifluoromethylphenyl | |
| 29 | 4 | 0 | 3-chlorophenyl | 85-90 |
| 30 | 4 | 0 | 3-fluorophenyl | |
| 31 | 4 | 0 | 3-trifluoromethoxyphenyl | |
| 32 | 4 | 0 | 3-tert.-butylphenyl | |
| 33 | 4 | 0 | 3-methylphenyl | |
| 34 | 4 | 0 | 3,4-dichlorophenyl | |
| 35 | 4 | 0 | 4-chlorophenyl | 112-115 |
| 36 | 4 | 0 | 2,5-dichlorophenyl | 68-73 |
| 37 | 4 | 0 | 2,4,5-trichlorophenyl | 120-125 |
| 38 | 4 | 0 | phenyl | 102-105 |

The 4,5-dimethoxypyridazones of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below:

I. 90 parts by weight of compound No. 1 is mixed with 10 parts by weight of N-methyl-alpha-pyrrolidone. A mixture is obtained which is suitable for application in the form of very fine drops.

II. 20 parts by weight of compound No. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound No. 10 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound No. 7 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound No. 29 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound No. 20 is intimately mixed with 97 parts by weight of particulate kaolin. A dust is obtained containing 3% by weight of the active ingredient.

VII. 30 parts by weight of compound No. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound No. 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The 4,5-dimethoxypyridazones of the formula I, or herbicidal agents containing them, may be applied pre- or postemergence. Preferably, the novel active ingredients or agents containing them are applied after emergence of the unwanted plants, both on crop-land and uncropped land. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the weather conditions, the plants to be combated and the growth stage of the plants, and varies from 0.05 to 10 kg/ha and more, but is preferably from 0.1 to 4.0 kg/ha.

The influence of 4,5-dimethoxypyridazones of the formula I on the growth of unwanted and crop plants is demonstrated in greenhouse experiments and experiments in the open.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. For this treatment, either plants which had been sown directly in the pots and grown there were selected, or plants which had been grown separately as seedlings and transplanted to the experiment vessels a few days before treatment. No covers were placed on the pots in this treatment method. The application rates for postemergence treatment varied from ingredient to ingredient, and were 0.25, 0.5, 1.0 and 3.0 kg of active ingredient per hectare.

The pots were set up in the greenhouse—species from warmer areas at from 20° to 35° C., and species from moderate climates at 10° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The experiments in the open were carried out on small plots in a soybean field, with naturally occurring weeds. The herbicidal agents were applied postemergence by means of a plot spray mounted on a tractor. Assessment was as in the greenhouse experiments.

The plants employed were *Abutilon theophrasti, Amaranthus retroflexus,* Amaranthus spp., *Arachys hypogaea, Cassia tora, Centaurea cyanus, Chenopodium album, Desmodium tortuosum, Echinochloa crus-galli, Galinsoga parviflora, Galium aparine,* Glycine max., Ipomoea spp., *Lolium multiflorum,* Polygonum spp., *Sinapis alba, Solanum nigrum, Triticum aestivum,* Viola spp., *Zea mays, Stellaria media, Avena fatua, Mercurialis annua, Oryza sativa,* and *Sorghum bicolor.*

On preemergence application in the greenhouse, for example compounds Nos. 2, 7, 10, and 20 had a herbicidal action.

On postemergence application in the greenhouse, for instance compounds Nos. 1, 2, 7, 10, 20 and 29 had a herbicidal action. On investigations into selective herbicidal action, compound No. 1, at 0.25 kg/ha, had a good herbicidal action on unwanted broadleaved plants, and crop plants such as groundnuts, Indian corn and wheat were only slightly and temporarily damaged, if at all. Compound No. 29 selectively combated broadleaved weeds at 0.5 kg/ha. At 1.0 kg/ha, compound No. 10 combated *Echinochloa crus-galli* in rice and had (as did compound No. 7) a herbicidal action on various other unwanted plants at 0.5 kg/ha, with only slight and temporary leaf damage to the crop plant Indian corn.

In the open, broadleaved weeds in soybeans were combated on postemergence application of 0.5 kg/ha of compound No. 1; only temporary scorching of the leaves of the crop plants occurred, and to an acceptable extent.

In view of the many application methods possible (preemergence treatment, postemergence foliage treatment, post-directed spraying), the active ingredients according to the invention, or agents containing them, may be used in numerous crops. Examples of such crops are given below.

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape seed |
| *Brassica napus* var. *napobrassica* | |
| *Brassica napus* var. *rapa* | turnips |
| *Brassica rapa* var. *silvestris* | |

| Botanical name | Common name |
| --- | --- |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the substituted 4,5-dimethoxypyridazones of the formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A substituted 4,5-dimethoxypyridazone of the formula

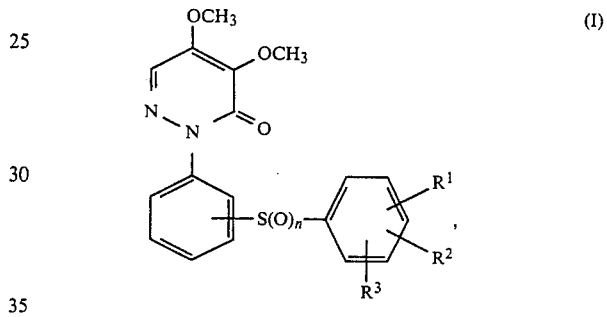

where $R^1$, $R^2$ and $R^3$ independently of one another are each hydrogen, halogen, nitro, cyano, carboxyl, alkyl of 1 to 4 c-atoms, haloalkyl of 1 to 4 c-atoms, alkoxy of 1 to 4 c-atoms, haloalkoxy of 1 to 4 c-atoms, alkylmercapto of 1 to 4 c-atoms, haloalkylmercapto of 1 to 4 c-atoms, alkylsulfinyl of 1 to 4 c-atoms, or alkylsulfonyl of 1 to 4 c-atoms, and n is 0, 1 or 2, wherein halo and halogen stand for fluorine, chlorine, bromine or iodine.

2. A substituted pyridazone of the formula I as claimed in claim 1, where

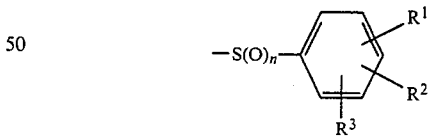

is in the 3- or 4-position on the phenyl ring, and $R^1$, $R^2$ and $R^3$ are in the 2,4,6-, 3,4,6- or 3,4,5-position and, independently of one another, are each hydrogen, halogen or haloalkyl of 1 to 4 carbon atoms.

3. 1-[3'-(2''-Chloro-4''-trifluoromethylphenylthio)-phenyl]-4,5-dimethoxypyridaz-6-one.

4. 1-[3'-(3''-Chloro-4''-trifluoromethylphenylthio)-phenyl]-4,5-dimethoxypyridaz-6-one.

5. A herbicide containing inert additives and an effective amount of a substituted 4,5-dimethoxypyridaz-6-one of the formula I as claimed in claim 1.

6. A herbicide as claimed in claim 5, containing a 4,5-dimethoxypyridazone of the formula I, where

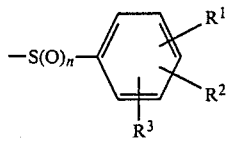

is in the 3- or 4-position on the phenyl ring, and $R^1$, $R^2$ and $R^3$ are in the 2,4,6-, 3,4,6- or 3,4,5-position and, independently of one another, are each hydrogen, halogen or haloalkyl of 1 to 4 carbon atoms.

7. A process for combating unwanted plant growth, wherein the unwanted plants or the areas to be kept free from unwanted plant growth are treated with a herbicidally effective amount of a substituted 4,5-dimethoxypyridazone of the formula I as claimed in claim 1.

8. A substituted pyridazone of the formula I as described in claim 1, wherein n is 0.

9. A substituted pyridazone of the formula I as described in claim 2, wherein n is 0.

10. A substituted pyridazone of the formula I as described in claim 1, wherein the group

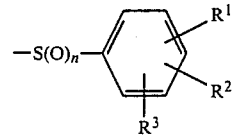

is in the 3- or 4-position on the phenyl ring, and $R^1$, $R^2$ and $R^3$ are each hydrogen, fluorine, chlorine or trifluoromethyl.

11. 1-[4'-(3''-chloro-4''-trifluoromethylphenylthio)-phenyl]-4,5-dimethoxy-pyridaz-6-one.

12. 1-[4'-(3''-trifluoromethylphenylthio)phenyl]-4,5-dimethoxy-pyridaz-6-one.

* * * * *